United States Patent
Van Wyck et al.

(10) Patent No.: US 10,380,322 B2
(45) Date of Patent: Aug. 13, 2019

(54) SYSTEM FOR ELECTRONICALLY ADMINISTERING HEALTH SERVICES

(71) Applicant: HealthFleet, Inc., Norwalk, CT (US)

(72) Inventors: William J Van Wyck, Darien, CT (US); Theresa Biasi, Shelton, CT (US); Anuja Ketan, Oxford, CT (US); Kelly Jura, Seymour, CT (US); Miranda McGill, Yorktown Heights, WI (US); Andre Roussel, Norwalk, CT (US)

(73) Assignee: Zillion Group, Inc., Norwalk, CT (US)

( * ) Notice: Subject to any disclaimer, the term of this patent is extended or adjusted under 35 U.S.C. 154(b) by 837 days.

(21) Appl. No.: 14/608,988

(22) Filed: Jan. 29, 2015

(65) Prior Publication Data
US 2016/0224752 A1    Aug. 4, 2016

(51) Int. Cl.
*G06F 19/00*    (2018.01)
*G06Q 10/10*    (2012.01)
*H04L 29/06*    (2006.01)

(52) U.S. Cl.
CPC ..... *G06F 19/3418* (2013.01); *G06Q 10/1095* (2013.01); *H04L 65/1069* (2013.01); *H04L 65/4076* (2013.01)

(58) Field of Classification Search
None
See application file for complete search history.

(56) References Cited

U.S. PATENT DOCUMENTS

| | | | | |
|---|---|---|---|---|
| 2006/0271399 | A1* | 11/2006 | Robson, Sr. | G06Q 10/0637 705/2 |
| 2007/0118389 | A1* | 5/2007 | Shipon | G06F 19/3418 379/203.01 |
| 2007/0174079 | A1* | 7/2007 | Kraus | G06Q 10/10 705/3 |
| 2007/0179925 | A1* | 8/2007 | Reid | G06F 19/3481 706/60 |
| 2012/0176466 | A1* | 7/2012 | Wrench | G06Q 10/101 348/14.07 |
| 2013/0239024 | A1* | 9/2013 | Lewis | H04N 7/147 715/756 |
| 2014/0088991 | A1* | 3/2014 | Bakes | G06F 19/3418 705/2 |
| 2014/0303988 | A1* | 10/2014 | Maneri | G16H 50/20 705/2 |
| 2016/0057391 | A1* | 2/2016 | Block | H04L 65/4023 348/14.07 |

OTHER PUBLICATIONS

I Cancer Health; 4 pages; Web-site www.medocity; Parsippany, NJ.

* cited by examiner

*Primary Examiner* — Michael Tomaszewski
(74) *Attorney, Agent, or Firm* — Boyle Fredrickson, S.C.

(57) ABSTRACT

The present inventors have determined that health services programs may be efficiently administered by providing a plurality of health services modules that are "horizontally integrated" on a platform. A rules engine is operative to identify enumerated events such that an event in one module triggers the rules engine to propagate a related event in one or more other modules. Such health services modules may be software architectural components operable for one or more of (1) live video conferencing, (2) scheduling, and/or (3) health services program data/content. Additional health services modules ("add-on modules") may also be provided on the platform and horizontally integrated.

21 Claims, 6 Drawing Sheets

SYSTEM FOR ELECTRONICALLY ADMINISTERING HEALTH SERVICES

BACKGROUND OF THE INVENTION

The present invention is directed to the field of health care, and more particularly, to a system for electronically administering health services for individuals provided by one or more entities.

Health services programs typically involve providing a variety of health related resources and content to individuals (users). Health services programs may address a variety of health concerns, such as weight loss, nutrition counseling, diabetes control, smoking cessation, pain management, stress reduction, depression counseling, addiction treatment, physical therapy, and the like. Resources for such programs may include providers (such as doctors, nurses, counselors, coaches) conducting live sessions with individuals, whether in person, by telephone, or otherwise, and individually or in groups; and delivering relevant content to individuals. Content may include: (1) informational articles (such as newsletters, reports, bulletins, recipes, exercises, e-mails, and blogs); (2) multimedia files (such as educational videos, pre-recorded webinars and audio tracks); and (3) interactive tools (such as health calculators, calendars, journals and trackers, such as for tracking weight, mood, exercise, and the like).

Health services programs may be tailored to individuals according to their age, health, gender and eligibility for benefits. With the recent implementation of the U.S. Affordable Care Act (ACA) of 2010, providing health services programs which ensure continuing/follow-on care for individuals is of heightened importance.

Today, providers may connect with individuals electronically (via the Internet), by telephone or in person. Providers may also deliver relevant content to individuals, such as via e-mail or websites. However, providers must typically operate within the limited framework of a host platform which provides such capabilities in a disassociated manner. For example, a provider may use a networked personal computer (PC) to access an electronic communication mechanism. The provider may then access a separate server to push content to the individual. Also, the provider may then access yet another server to record notes, update scheduling information and/or perform other administrative tasks. However, switching between these environments oftentimes leads to inefficiency and potentially risks update errors.

In addition, individuals may undergo multiple "change-in-life" events over time. Change-in-life events can include, for example, changing one's name, marital status, listing of dependents, employment, insurance, health status, and so forth. As a result, providing a health services program to the same individual over time, including tracking the individual's progress, is challenging. Adding to this difficulty, health information itself also typically requires security and safe handling to ensure patient privacy. For example, the U.S. Health Insurance Portability and Accountability Act of 1996 (HIPAA) establishes certain guidelines for the secure treatment of Protected Health Information (PHI).

What is needed is an improved mechanism for more efficiently performing the necessary tasks for administering a health services program. Also, a mechanism for providing health services program to individuals, despite change-in-life events, is needed.

This background information is provided to reveal information believed by the applicant to be of possible relevance to the present technology. No admission is necessarily intended, nor should be construed, that any of the preceding information constitutes prior art against the present technology.

SUMMARY OF THE INVENTION

The present inventors have determined that health services programs may be efficiently administered by providing a plurality of health services modules that are "horizontally integrated" on a platform. A rules engine is operative to identify enumerated events such that an event in one module triggers the rules engine to propagate a related event in one or more other modules. Such health services modules may be software architectural components operable for one or more of (1) live video conferencing, (2) scheduling, and/or (3) health services program data/content. Additional health services modules ("add-on modules") may also be provided on the platform and similarly horizontally integrated, such as for (1) daily check-in, (2) managing medications, (3) updating/monitoring health number, (4) social access, and/or (5) rewards.

As used herein, "horizontally integrated"/"horizontal integration" refers to connections between modules at a common hierarchy level such that an update in one module propagates a related update in another module. Integration of the aforementioned modules results in an enabled platform that is readily portable to host platforms and optimized for delivering health services programs with increased efficiency. Horizontal integration is accomplished using a rules engine connected to each module which is configured to monitor enumerated events in the modules and propagate a change in other module corresponding to the enumerated event. Integrations include the ability to link various modules into a curriculum of care and coaching, for a cohesive program that incorporates various modules for the optimization of outcomes through the education and influence of patients and plan members.

Module updates may be propagated as follows: (1) selecting disease management or health content via health services program data may initiate scheduling with providers for counseling sessions or classes, and may initiate countdowns, reminders and/or a "start now" link for video conferencing; (2) selecting scheduling data may initiate delivery of particular health content, and may initiate countdowns, reminders and/or a "start now" link for video conferencing; and (3) selecting video conferencing may initiate delivery of particular health content (such as a provider pushing an article), may provide optional recording of video conferencing data (such as a recorded mp3 or an automated transcript), may capture the call date/time, duration, completion, attendees or the like in scheduling data, and/or may trigger a follow up appointment in scheduling data. The modules may be integrated using API interfaces and may tie in to a host platform providing health content and scheduling information via embedded service calls.

In addition, "unique identification codes" may be associated with (1) classes of health services programs or "health cubes," and (2) health information about particular individuals possessing the unique identification codes. Moreover, unique identification codes may be linked to health services programs and related content for individuals groups of health programs, qualification criteria and pricing specified by specific clients. By determining common relationships between health information associated with differing identification codes, the identification codes can be linked to persistently provide health benefits for the same individual over time, despite changes in codes. Also, by associating a measurement result specific to an individual with a unique identification code, specific programs based the measurement result can be recommended, and participation by individuals can be encouraged. Participation and use of modules creates track-able and reportable activities that can be leveraged in analytics and reporting, for purposes such as incentives management and progress reporting.

The system may be deployed in scalable environments, such as via cloud computing, to provide cost-effective program offerings. Accordingly, by integrating embodiments of the present invention, host platforms may deliver health programs while focusing on the quality of the health benefit offerings. Integration can be achieved via portable modules making Application Program Interface (API) calls or via white label pages that may be embedded.

The system may also utilize Java Script Object Notation (JSON), Representational State Transfer (REST) and/or other standards, architectural styles or techniques to provide integration capability with host platforms. In addition, information can be advantageously extracted via pre-prepared reports, such as via Extensible Markup Language (XML), Extensible Stylesheet Language Transformations (XSLT) and/or XML Schema Definition (XSD) files.

The system may also provide Data as a Service (DaaS) by storing health information about individuals and/or related aspects. Configurable data analytics and quantitative and qualitative analysis results may also be determined and made available, such as via secure reports and/or API calls.

It is also contemplated to provide a curriculum building program for easily creating and defining health services activities or other assets, grouping such assets into an event, including with notifications, incentives, and so forth, and arranging such events along a program timeline. The combination of content and delivery as prescribed in an administrator designed engagement curriculum is a unique approach for scripting partial and total experiences for individuals and groups of individual users.

Specifically, one aspect of the invention may provide a horizontally integrated system for administering a health services program executable on an electronic computer according to a program stored in a non-transient medium to implement: a plurality of modules, including: (a) a video conferencing module configured to enable live video conferencing over a computer network; and (b) a health services module configured to index a plurality of health services content; and a rules engine in communication with each of the plurality of modules. The rules engine may be configured to provide an update to at least one of the plurality of modules according to an event that occurs in another of the plurality of modules.

The plurality of modules could also include a scheduling module configured to receive scheduling information relating to a plurality of time slots for health services. The plurality of modules could also include one or more "add-on" modules.

Another aspect may provide a method for administering a health services program from an electronic computer providing a video conferencing module configured to enable live video conferencing sessions over a computer network, a health services module configured to index a plurality of health services content, and a scheduling module configured to receive scheduling information relating to a plurality of time slots for health services. The method may include: (a) monitoring an event that occurs in a first module, the first module being at least one of the video conferencing module, the health services module and the scheduling module; and (b) providing an update in a second module according to the event, the second module being at least one of the video conferencing module, the health services module and the scheduling module.

Another aspect may provide a system for building a curriculum for providing health services, the system executable on an electronic computer according to a program stored in a non-transient medium to: (a) provide a first health services program that includes a first set of health services activities; (b) provide a second health services program that includes a second set of health services activities, the second health services program different from the first health services program; and (b) graphically display the first and second sets of health services activities with respect to a common timeline.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENT

System Architecture

Figure 1:
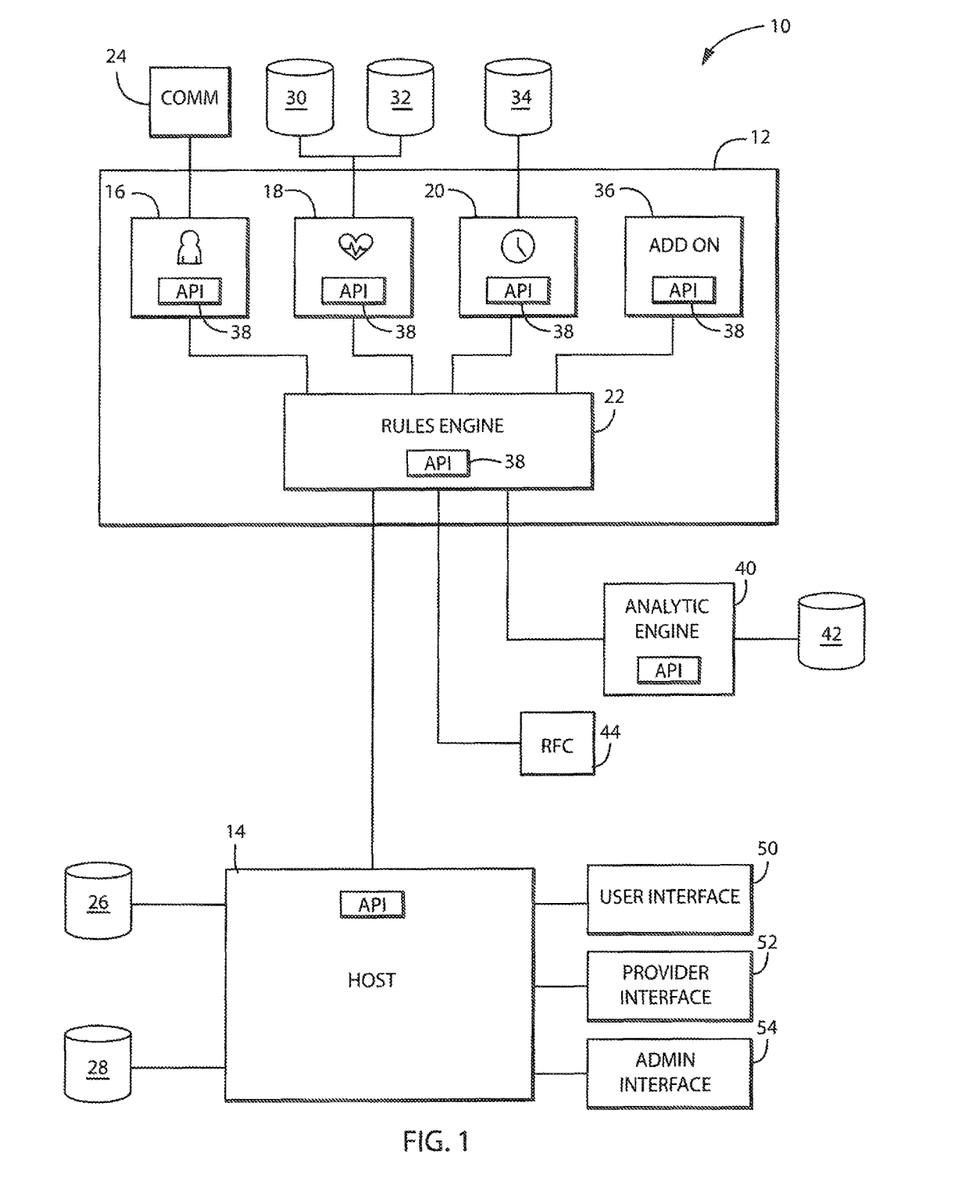
FIG. 1 is a block diagram illustrating a horizontally integrated system for administering a health services program in communication with a host platform in accordance with an embodiment of the invention.

Referring now to FIG. 1, a computing environment 10 includes a horizontally integrated system 12 for administering a health services program in accordance with an embodiment of the invention. The horizontally integrated system 12 may be implemented, for example, via a cloud computing server, a private cloud or intranet server, or private desktop, and may be in communication with a host system 14. The horizontally integrated system 12 includes a plurality of modules, including a video conferencing module 16, a health services module 18 and a scheduling module 20. The video conferencing module 16, the health services module 18 and the scheduling module 20 may be software architectural components operable for computing functions including live video conferencing, indexing health services program data/content and scheduling, respectively. A rules engine 22 is in communication with each of the plurality of modules.

The video conferencing module 16 is configured to enable live video conferencing over a computer network such as the Internet. The video conferencing module 16 may implement an Internet telephony architecture which may be based on a peer-to-peer connection scheme. The video conferencing module 16 may open multiple ports via communications port 24 to enable communications with multiple clients, which may correspond to individuals (users) and providers (doctors, nurses, counselors, coaches, and the like), among multiple simultaneous sessions. Accordingly, video conferencing sessions may be one-to-one (such as a private counseling session between an individual and a provider) or one-to-many (such as a group session led by a provider with multiple attendees in which many attendees can see and talk to the provider and/or each other during sessions).

The health services module 18 is configured to index a plurality of health services content. As such, the health services module 18 may communicate with the host system 14, via the rules engine 22, to retrieve raw health services programs and content data which may be stored in a host platform content database 26. Health services programs may include a variety of content pre-arranged by the host for addressing various health concerns such as weight loss, nutrition counseling, diabetes control, smoking cessation, pain management, stress reduction, depression counseling, addiction treatment, physical therapy, and the like. Content may include: (1) informational articles (such as newsletters, reports, bulletins, recipes, exercises, e-mails, blogs, and the like); (2) multimedia files (such as educational videos, pre-recorded webinars or audio tracks, and the like); (3) interactive tools (such as health calculators, calendars or journals), and the like.

As described below with respect to FIG. 2, the health services module 18 may use a first data structure 30 (which could be separately stored) to link "unique identification codes" to "health cubes" including health services programs and related content for individuals. In addition, as described below with respect to FIG. 4, the health services module 18 may use a second data structure 32 (which could be separately stored) to link the unique identification codes to health information about individuals possessing the unique identification codes. Upon receiving a unique identification code from an individual, the health services module 18 may determine programs and content eligible to the individual based on the health cube and health information linked to the unique identification code. Accordingly, the rules engine 22 may operate to limit the health services module 18 to delivering content according to the unique identification code which may be set by eligibility status.

The scheduling module 20 is configured to receive scheduling information relating to a plurality of time slots for health services. Accordingly, the scheduling module 20 may communicate with the host system 14, via the rules engine 22, to retrieve raw scheduling and calendaring data which may be stored in a host platform scheduling database 28. This may include time slots on given dates by particular providers for particular topics. For example, one health coach may have a 30 minute time slot available four times a week for smoking cessation, while another health coach may have a 45 minute time slot two times a week for diabetes control.

The scheduling module 20 may use a local data structure 34 (which may be separately stored) for indexing scheduling data for providers and maintaining a virtual calendaring and appointment system. Accordingly, the scheduling module 20 may allow an individual to view time slot availabilities (by times and dates) for the various providers and/or various subjects of interest. For example, an individual may find, via the scheduling module 20, a time slot for a particular pain management coach or a next available pain management coach, and may request an appointment accordingly. Requesting the appointment may temporarily hold the time slot reserved while the scheduling module 20 executes to confirm eligibility, confirm availability, request/secure payment, finalize the appointment and/or send notifications.

The rules engine 22, in communication with each of the plurality of modules, is configured to provide an update to the video conferencing module 16, the health services module 18 and/or the scheduling module 20 according to monitored events that occurs in other modules. In other words, the rules engine 22 may identify an enumerated event in a first module, such that the event triggers the rules engine to propagate a related event in a second, thereby providing horizontal integration between the first and second modules.

By way of example, a video conferencing session via the video conferencing module 16 may be an event which triggers the rules engine 22 to update the scheduling module 20, such as to record a completion of the video conferencing session on the particular date/time with a particular duration, or which triggers the rules engine 22 to update the health services module 18 to deliver content to an individual that is related to the video conferencing session (such as a nutrition article related to a diabetes control session). Similarly, a selection of a time slot via the scheduling module 20 may be an event which triggers the rules engine 22 to update the health services module 18 to deliver or otherwise make available content related to the selection back to the individual, or which triggers the rules engine 22 to update the video conferencing module 16 to initiate a timer according to the selection of the time slot, which could serve as a continuous reminder or countdown the session, followed by a button to automatically launch the session. Likewise, a selection of content via the health services module 18 may be an event which triggers the rules engine 22 to update the video conferencing module 16 to suggest a video conferencing session to join (such as a selecting a tobacco article leading to suggestion to join a smoking cessation session), or may be an event which triggers the rules engine 22 to update the scheduling module 20 to suggest a time slot, such as for a particular provider or health subject, related to the selection (such as a selecting a tobacco article leading to a suggestion to schedule a time with a smoking cessation counselor).

Accordingly, the rules engine 22 enables connections between the aforementioned modules at a common hierarchy level such that an update in one module propagates a related update in another module. Integration of the aforementioned modules results in an optimized platform that is readily portable to host platforms, including those with user/provider ports and raw content, such as the host system 14.

Additional health services modules ("add-on modules") may also be provided on the horizontally integrated system 12 within the spirit of the invention. For example, an add-on module 36 may be simultaneously or subsequently deployed to the horizontally integrated system 12 to provide additional functionality. The rules engine 22 may have predefined hooks for monitoring events and propagating updates for various possible add-on modules, and/or the rules engine 22 may be updated, such as in software or firmware, to utilize new hooks for monitoring events and propagating updates. Examples of the add-on module 36 include: (1) a daily check-in module; (2) a managing medications module; (3) an updating/monitoring health number module; (4) a social access module; and/or (5) a rewards module. Additional aspects of the aforementioned modules are described with respect to FIGS. 7 and 8.

The rules engine 22 and the aforementioned modules may each include an Application Program Interface (API) element 38 for enabling cross communication and/or exposing integrated functionality. The API element 38 may also facilitate portability of the horizontally integrated system 12 for connection with the host system 14.

The rules engine 22 may also be in communication with an analytic engine 40. The analytic engine 40 may provide interactive functionality directed toward reporting and analytics for managers and executives. The analytic engine 40 may include an API element 38 for communicating with other modules, and may communicate with an analytic data structure 42 for mass information storage, and/or for exposing integrated functionality. Accordingly, the analytic engine 40 may provide Data as a Service (DaaS) and may allow, among other things, out of the box reports for executives and managers; data analytics with point and click access to various cross sectional information; and support for information storage or data warehousing for extended periods, such as greater than seven years.

In the environment 10, the horizontally integrated system 12, via the rules engine 22, may also be in communication with a real time clock (RTC) 44 or another precision time protocol element. The RTC 44 may provide close synchronization between the aforementioned modules.

In embodiments, the rules engine 22 may also allow, among other things, providing industry standard authentication protocol information for sharing across enterprise platforms, such as in accordance with open standard for authorization (OAuth) 1.0; authenticating and updating profiles and branding information of health systems, providers, insurers, agents, brokers or employers; authenticating and updating profile information of counselors; configuring privileges given to organizations, members and counselors to obtain access to other modules; providing internal accounting, accounts payable and receivables for billing and invoicing; implementing extracts, transfers and loads (ELF) of information to and from external systems such as incentives management, claims management, pharmacies and electronic medical record (EMR) systems; providing dynamic content publishing, such as of articles, recipes and videos; and providing alerts and notifications sent via e-mail and/or Short Message Service (SMS) text messaging during various stages of workflow.

The horizontally integrated system 12 may be deployed in scalable environments, such as cloud computing, a private cloud or intranet, or a private desktop, to provide cost-effective program offerings. The horizontally integrated system 12 could be provided via "Software as a Service" (SaaS), and embodiments may also utilize JSON, REST and/or other standards, architectural styles or techniques to provide integration capability with host system 14 as known in the art. In addition, information in the modular architecture can be advantageously extracted via pre-prepared reports, such as via XML, XSLT and/or XSD files.

In operation, the host system 14 may deliver content to the horizontally integrated system 12, such as from the host platform content database 26 and the host platform scheduling database 28. An individual or user may then access the host system 14 via a user interface 50. Similarly, a provider may access the host system 14 via a provider interface 52, and an administrative agent may access the host system 14 via an admin interface 54. Differing access points allow differing access rights and privileges in the environment 10, with the admin interface 54 essentially allowing maintenance ability. Moreover, each access point may be customized with respect to its own sets of rights and privileges. For example, various levels of the provider interface 52 may grant access to specific pieces of an individual's information based on permissions granted to the provider by the client or entity. Accordingly, a health coach, for example, might see all of an individual's information, including personal health information, via the provider interface 52, while a case manager might only see contact and status information via the same provider interface 52.

The host system 14 may provide front end interfaces to users and providers, such as external web site access via the user interface 50, and internal web site access via the provider interface 52. The host system 14 then receives requests from the user interface 50 and/or the provider interface 52, and forwards the requests to the horizontally integrated system 12 for processing. The horizontally integrated system 12, in turn, processes the requests and returns processed data to the host system 14 for serving to the user interface 50 and/or the provider interface 52.

Data Flow

Figure 2:
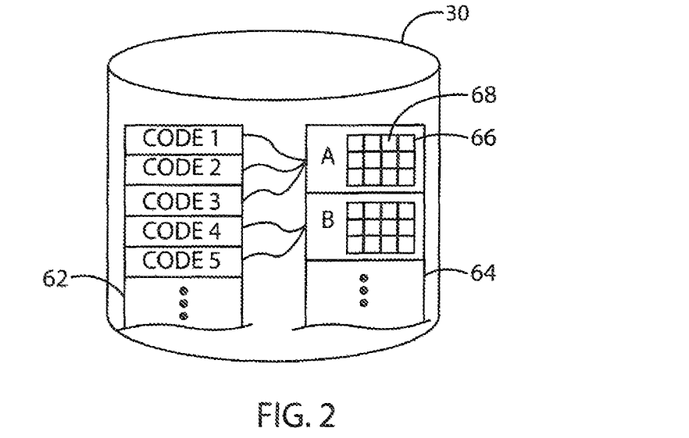
FIG. 2 is a diagram illustrating a first data structure linking unique identification codes to health cubes in accordance with an embodiment of the invention.

Referring now to FIG. 2, a diagram illustrating the first data structure 30 linking unique identification codes 62 to health cubes 64 which include health services programs and related content for individuals is provided in accordance with an embodiment of the invention. The unique identification codes 62 may include any number of data patterns of varying configurations and length. For example, in an embodiment, alpha numeric patterns, such as "33-AQR-54665" or "MZ-4XMZ-U9F," may be used.

The health cubes 64 may represent classes of structured health services programs 66, each including a plurality of pre-approved, relevant content 68. Health services programs 66 may represent structured curriculums for a variety of health subjects, such as weight loss, nutrition counseling, diabetes control, smoking cessation, pain management, stress reduction, depression counseling, addiction treatment, physical therapy, and the like. Pre-approved, relevant content 68 for each program may include: (1) informational articles (such as newsletters, reports, bulletins, recipes, exercises, e-mails, blogs, and the like); (2) multimedia files (such as educational videos, pre-recorded webinars or audio tracks, and the like); (3) interactive tools (such as health calculators, calendars or journals); and (4) scheduling for live sessions.

The health cubes 64 are divided according to categories, tiers or groups, such as groups "A," "B" and "C," which provide health services programs and content for individuals with identification codes associated with the group. Associations may be configured, for example, based on health insurance benefits that individuals are eligible to receive. In addition, or alternatively, content 68 of the health cubes 64 may be unstructured or free from particular health services programs 66. By way of example, as illustrated in FIG. 2, "Code 1," "Code 2" and "Code 3" may be linked to health cube "A" for a first set of health services programs and content, while "Code 4" and "Code 5" may be linked to health cube "B" for a second set of health services programs and content. Accordingly, Codes 1, 2 and 3 may be provided to three individuals associated with a first employer, while Codes 4 and 5 may be provided to two individuals associated with second employer.

Figure 3:
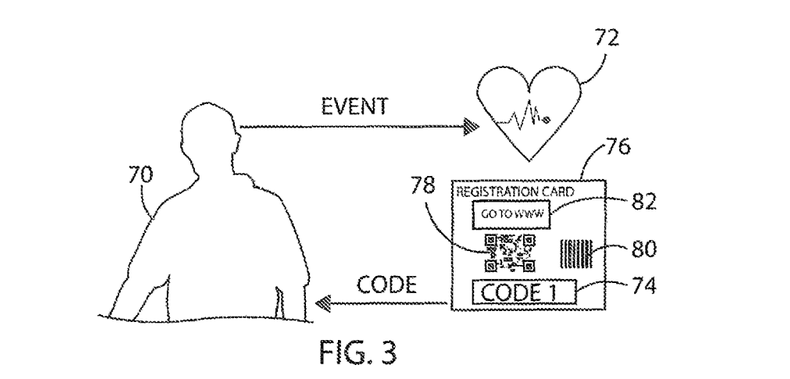
FIG. 3 is a diagram illustrating an exemplar mechanism for providing unique identification codes to individuals in accordance with an embodiment of the invention.

Referring now to FIG. 3, a diagram illustrating an exemplar mechanism for providing unique identification codes to individuals is provided in accordance with an embodiment of the invention. An individual 70 may participate in an event which produces a measurement result 72 specific to the individual 70. For example, the individual 70 may be part of group in which many individuals have their blood pressure, height/weight, eyesight or other health related characteristics measured.

Next, a unique identification code 62 is provided to the particular individual 70, such as a registration card 76 prompting the individual 70 to take action to register the unique identification code 62. The registration card 76 may include, for example, a uniform resource locator (URL) or web address prompting the individual 70 to go online, such as to the host system 14 via the user interface 50, to submit the unique identification code 62 for registration. In addition, or alternatively, the registration card 76 may include a quick response (QR) code 78, a bar code 80 and/or any other indicia for the individual 70 to scan, such as via a smart phone or tablet, for faster action to register the unique identification code 62. The individual 70 may be encouraged to do so, for example, to receive the measurement result 72, reports or analyses relating to the measurement result 72 and/or program data or content associated with the measurement result 72. The registration card 76 may also include health information 82 about the individual 70, such as the individual's name or employer, as well as information about the provider.

The unique identification code 62 and/or the registration card 76 may be mailed, e-mailed, personally delivered, or otherwise distributed to the individual 70. In addition, unique identification code 62 and/or the registration card 76 could also be provided without participation in an event and/or without the measurement result 72. However, participation in an event and/or producing the measurement result 72 may be effective tools for encouraging participation by the individual 70.

Alternatively, eligibility lists may be provided which can be checked, for example, during a registration process. As such, codes assigned to a client may then, in turn, be assigned to individual payers.

Figure 4:
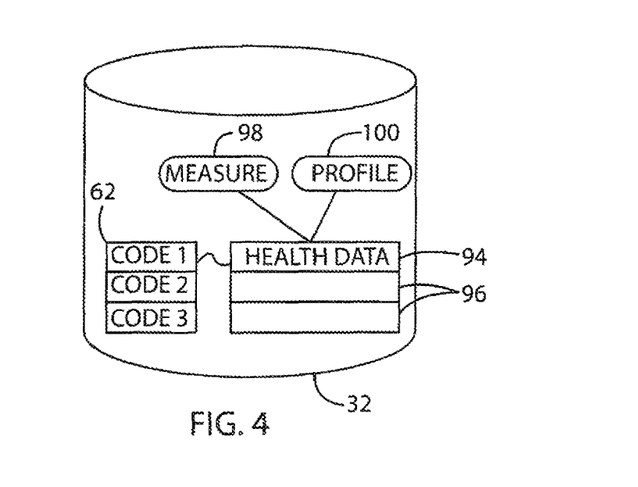
FIG. 4 is a diagram illustrating a second data structure for linking unique identification codes to health information of individuals in accordance with an embodiment of the invention.

Referring now to FIG. 4, a diagram illustrating the second data structure 32 linking unique identification codes 62 to health information of individuals possessing the unique identification codes is provided in accordance with an embodiment of the invention. Health information about individuals, such as that collected during the event described with respect to FIG. 3, is then linked to the unique identification code 62. For example, health information 94 corresponding to health data about the individual 70 may be linked to "Code 1." In addition, data spaces 96 may be reserved for linking health information about other individuals to other unique identification codes. The health information 94 may comprise a first data element 98 corresponding to the measurement result 72 and a second data element 100 corresponding to personally identifiable information and/or protected health information about the individual, such as the health information 82. Accordingly, programs and content eligibility may be determined for an individual, and limited accordingly, based on the health cube and health information linked to the unique identification code.

If an individual has been in different programs, such as via the same or different clients or entities providing codes, the individual can be linked via common health information associated with the codes. For example, if multiple codes are determined to be associated with common personally identifiable information, those codes may be linked such that current and future information about an individual is accurately maintained.

Curriculum Building

A curriculum building process provides for easily creating and defining health services activities or other assets, grouping such assets into one or more events, including with notifications, incentives, and so forth, and arranging such one or more events along a program timeline. Accordingly, the combination of content and delivery as prescribed in an administrator designed engagement curriculum is a unique approach for scripting partial and total experiences for individuals and groups of individual users.

Figure 5:
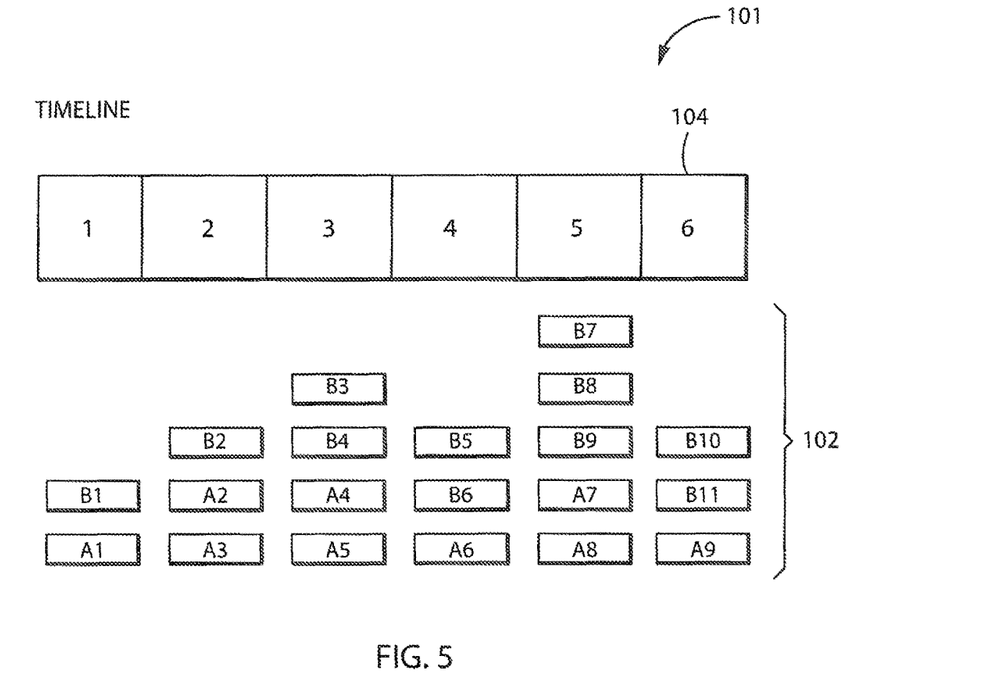
FIG. 5 is a diagram illustrating a plurality of health services activities, including content and time slots, arranged with respect to a timeline via a graphical display in accordance with an embodiment of the invention.

Referring now to FIG. 5, a diagram 101 illustrates a plurality of health services activities 102, including content and time slots, arranged with respect to a common timeline 104 via a graphical display in accordance with an embodiment of the invention. When an individual selects a program 66, content 68 with respect to the program may be graphically displayed to the individual over the timeline 104 via the rules engine 22. This may be particularly useful for work load balancing, particularly when multiple programs are enrolled.

For example, a user may select enrollment in a first program "A" which may correspond to diabetes control. As a result, a first set of health services activities denoted "A1" through "A9" may appear as ticks, marks or other notations that are individually mapped with respect to the timeline 104 which may represent weeks. In week 1, health services activity A1 may correspond to a live video conferencing session with a diabetes counselor, in week 2, health services activity A2 may correspond to another live video conferencing session with a diabetes counselor, and health services activity A3 may correspond to content for review, such as an informational article; and so forth. The user may also select enrollment in a second program "B," which may correspond to smoking cessation. As a result, a second set of health services activities denoted "B1" through "B11" may also appear as ticks, marks or other notations that are individually mapped with respect to the timeline 104. Also, the second set of health services activities B1 through B11 may be displayed with the first set of health services activities A1 through A9 on the timeline 104 to illustrate load balancing.

The health services activities 102 may be color coded to correspond to an activity type. For example, health services activities 102 corresponding to live video conferencing sessions may be orange, health services activities 102 corresponding to content may be red, and so forth. Moreover, the health services activities 102 may each be hyperlinks or other points of access for further information about the respective activity, such as via the modules of the horizontally integrated system 12.

In addition, a client or entity may define a permissible set of live session types and allow a member to request a session that is not defined as part of a program. For example, a member could be in a program with a defined set of events, and also be allowed to request an additional event, such as a live session with a counselor, that is not defined as part of the program. The additional event could be provided, for example, for a fee or complimentarily.

Also, the curriculum design allows for the rules engine 22 to update the rules engine update health services activities according to events that occur in one or more of the modules. For example, notifications, alerts and/or incentives may be automatically applied to curriculum components such as health services activities 102. A data structure, such as a reference table, may be maintained for tracking such updates, including notifications, alerts and/or incentives, and communicating with other modules of the horizontally integrated system 12.

System Environment

Figure 6:
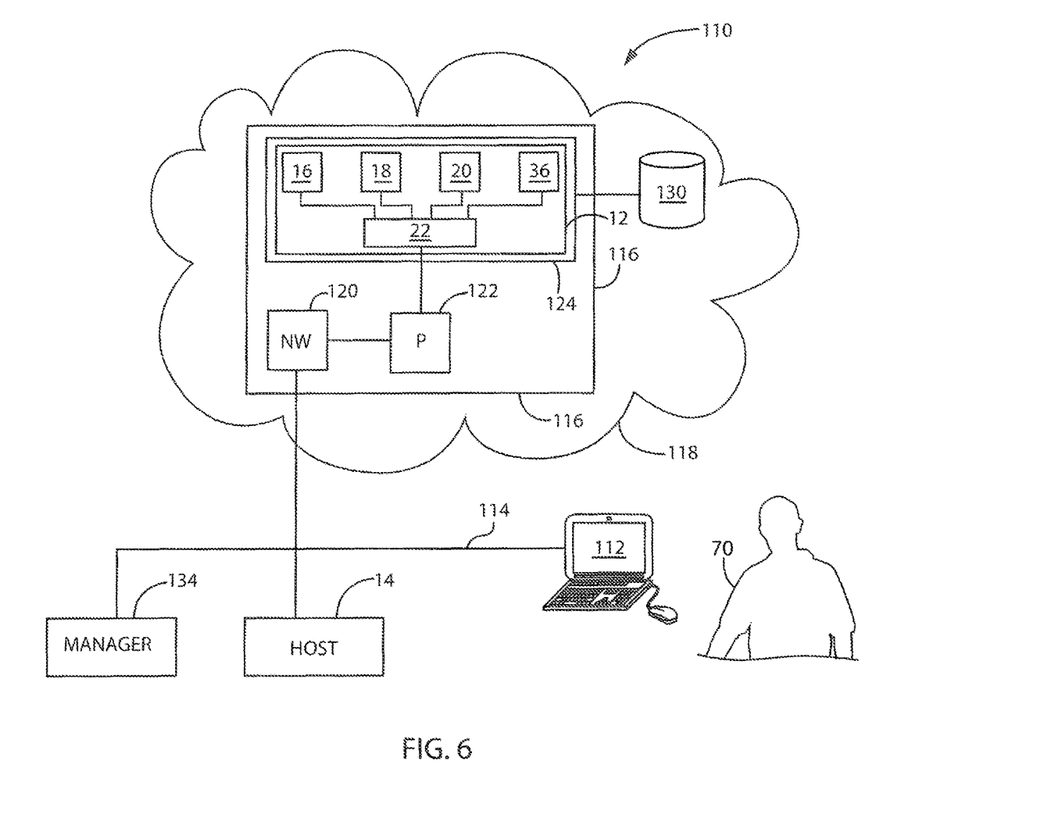
FIG. 6 is a block diagram illustrating operation of the horizontally integrated system of FIG. 1 in a system environment.

Referring now to FIG. 6, a block diagram illustrating operation of the horizontally integrated system 12 in a system environment is provided in accordance with an embodiment of the invention. The individual 70 may use a computer 112, smart phone, tablet or other computing device to access, via a computer network 114 (which may be the Internet), the host system 14. In an SaaS configuration, the host system 14 may then, in turn, access a cloud computing environment 118 (or alternatively, a private cloud or intranet or desktop). The cloud computing environment 118 may include a server 116 which includes a network interface 120, a processor 122 and a non-transient memory 124 for executing the horizontally integrated system 12 as described above with respect to FIG. 1. The server 116 may also be in communication with a mass storage 130 for holding the first data structure 30, the second data structure 32, and the like.

The host system 14 may provide a host company's website, for example, and communicate with the horizontally integrated system 12 via API's or embedded service calls. In an alternative arrangement, the horizontally integrated system 12 may be directly integrated in the host system 14, or may be distributed over multiple computer systems. A separate manager system 134 may also be provided for admin access and maintenance ability.

In operation, the individual 70 may navigate to the host system 14 and submit a unique registration code via the user interface 50. The host system 14 may, in turn, forward the unique registration code to the server 116. The server 116 may, in turn, execute, for example, the health services module 18 to register the individual 70. The server 116 may then execute to display a measurement result specific to the individual 70 to the computer 112, and may determine and display a program data and content relevant to the measurement result and the individual 70. For example, if the measurement result relates to a vision test, the server 116 could execute to provide a visual acuity result to the individual 70 and an analysis of the result as compared to age or peers, in addition to a vision insurance benefit for eyeglasses, a newsletter concerning maintaining good eye health, an advertisement for discounts on eyeglasses, and so forth.

The individual 70 may proceed to obtain allowable content via the health services module 18. The individual 70 may also proceed to schedule time slots via the scheduling module 20. The individual 70 may also proceed to engage in live video conferencing session via the video conferencing module 16. The individual 70 may also view health services activities 102 with respect to a time line for work load balancing via the computer 112.

User Experience

Figure 7:
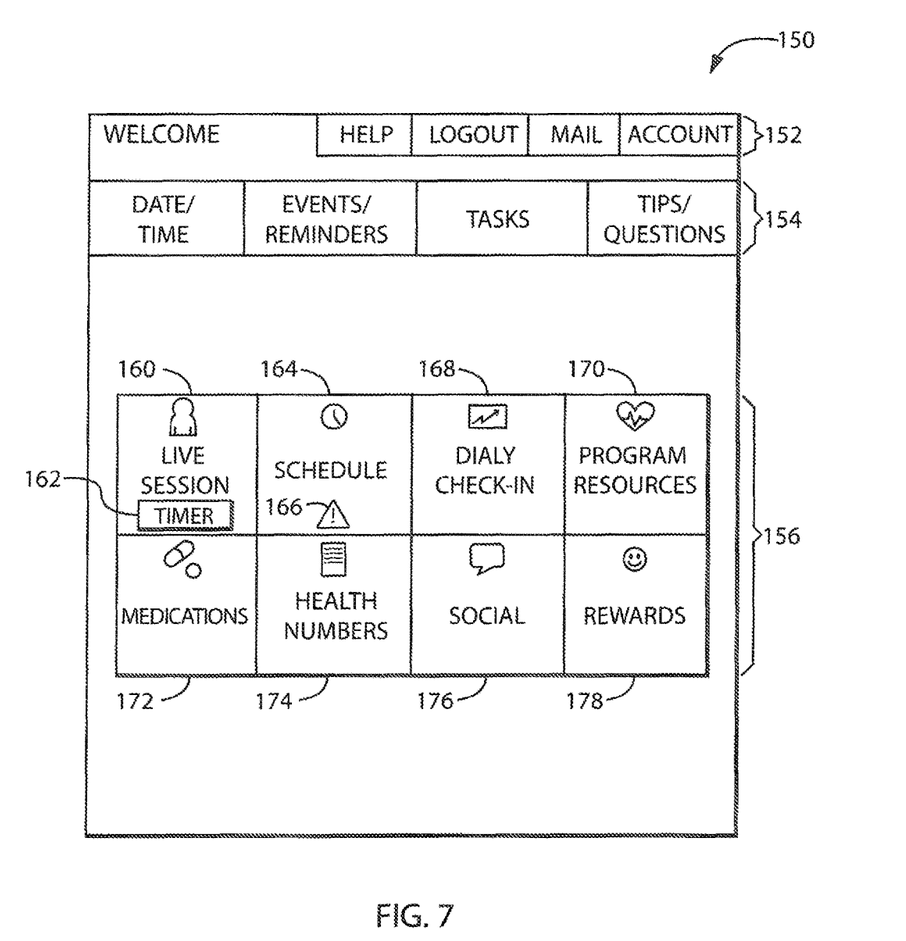
FIG. 7 is a diagram illustrating a graphical view for delivery of the health services program of FIG. 1 to an individual.

Referring now to FIG. 7, a diagram illustrating a first graphical view 150 for delivery of the health services program of FIG. 1 to an individual thereby providing a user experience is provided in accordance with an embodiment of the invention. Upon authentication of a unique identification code or proper login credentials, the individual 70 may be presented with the first graphical view 150 via the computer 112. The first graphical view 150 may include a welcome screen with a header 152 followed by a banner 154. The header 152 may include links for obtaining help, obtaining mail messages, accessing account settings, logging out and/or similar functions. The banner 154 may include links indicating the time and date, upcoming events and reminders, pending tasks for the individual, health tips for the individual, and/or a quick pulse question for the individual (relating, for example, to mood, opinion or knowledge). An area below graphically displays a plurality of tiled links 156 generally relating to the implemented modules of the horizontally integrated system 12. The links may appear, for example, as a plurality of tiled icons.

For example, a first tiled link 160, which may be titled "Live Session," may relate to the video conferencing module 16. An active timer 162 may be actively displayed over the first tiled link 160 to serve as a countdown (and continuous reminder) for the next live video conferencing session. Clicking on the active timer 162 during the countdown may be an event in the video conferencing module 16 which triggers the rules engine 22 to display scheduling information for the next live video conferencing session to the graphical display via the scheduling module 20. When it is time to join a next video conferencing session, the timer 162 may transition to a "Join Now" link to initiate the video conferencing session when clicked. Accordingly, the rules engine 22 may monitor events from and provide updates to video conferencing module 16 as described above with respect to FIG. 1.

A second tiled link 164, which may be titled "Schedule," may relate to the scheduling module 20. Scheduling indicia 166 may be actively displayed over the second tiled link 164 to serve as a notification of a pending scheduling activity for a time slot. Accordingly, the rules engine 22 may monitor events from and provide updates to the scheduling module 20 as described above with respect to FIG. 1.

A third tiled link 168, which may be titled "Daily Check-In," may relate to the daily check-in module, which may be an add-on module. The daily check-in module may provide, for example, information relating to goals, notes, journal activity, ail so forth, and may link to other modules which may provide related content. Accordingly, the rules engine 22 may monitor events from and provide updates to the daily check-in modul.

A fourth tiled link 170, which may be titled "Program Resources," may relate to the health services module 18. Accessing the health services module 18 may allow access to programs and content which may include links, for example to scheduling and video conferencing sessions. Accordingly, the rules engine 22 may monitor events from and provide updates to the health services module 18 as described above with respect to FIG. 1.

A fifth tiled link 172, which may be titled "Medications," may relate to the managing medications module, which may be an add-on module. The medications module may allow inputting and tracking medications. Certain medications could trigger the rules engine 22, for example, to propose a video conferencing session, a time slot or content related to the medication, or provide a reward, via the rewards module, for consistently taking the medication. Accordingly, the rules engine 22 may monitor events from and provide updates to the social access module.

A sixth tiled link 174, which may be titled "Health Numbers," may relate to the updating/monitoring health number module, which may be an add-on module. The updating/monitoring health number module may allow entering health numbers, such as cholesterol levels, triglyceride levels, blood pressure, weight, and so forth, for tracking and monitoring over time. Certain health numbers could trigger the rules engine 22, for example, to propose a video conferencing session, a time slot or content, such as a stress reduction program and content for consistently high blood pressure levels. Accordingly, the rules engine 22 may monitor events from and provide updates to the updating/monitoring health number module.

A seventh tiled link 176, which may be titled "Social," may relate to the social access module, which may be an add-on module. The social access module may allow sharing updates or links with others, for example, as a link to content from the health services module 18. Accordingly, the rules engine 22 may monitor events from and provide updates to the social access module.

An eight tiled link 178, which may be titled "Rewards," may relate to the rewards module, which may be an add-on module. The rewards module may track incentives, such as cash rewards and discounts, for various events, such as attending video conferencing sessions, viewing content, and so forth. Accordingly, the rules engine 22 may monitor events from and provide updates to the rewards module.

Figure 8:
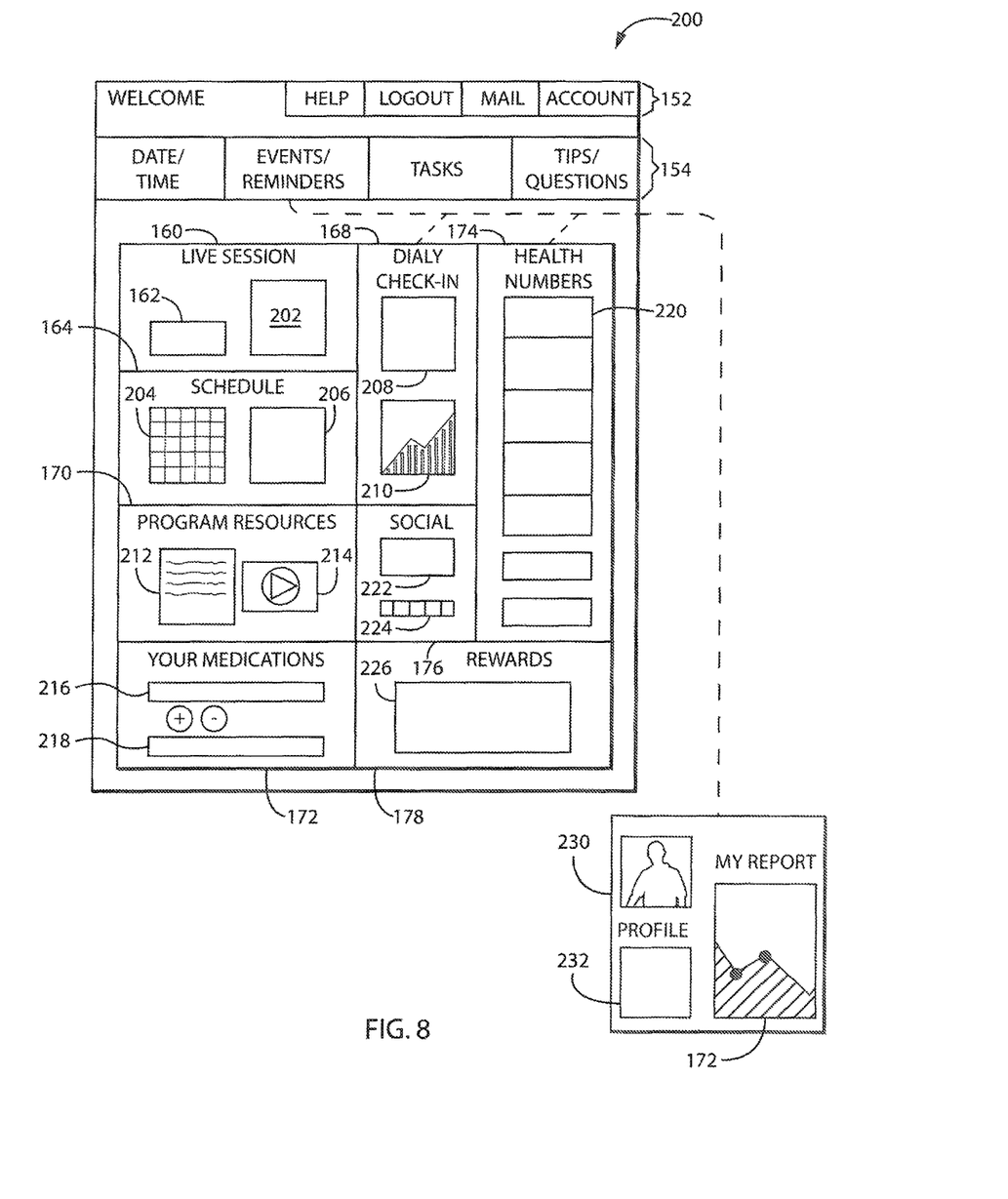
FIG. 8 is a diagram illustrating expanded tiles of the graphical view of FIG. 7.

Referring now to FIG. 8, a diagram illustrating expanded tiles of a second graphical view 200 is provided. The individual 70 could swipe across screens between the first and second graphical views 150 and 200, respectively, selecting one or more of the aforementioned tiled links to dynamically display more information associated with the tiled links. For example, the first tiled link 160 ("Live Session") may include the timer 162, now timing a duration of an active video conferencing session, and a communications window 202 for the video conferencing. The second tiled link 164 ("Schedule") may include a calendar 204 and an appointments/reminders area 206 for highlighting upcoming appointments and reminder times. The third tiled link 168 ("Daily Check-In") may include a goals/notes area 208 for tracking goals and recording notes and an activity tracker 210. The fourth tiled link 170 ("Program Resources") may include a links area 212 to a plurality of programs and content, as well as a multimedia area 214 for viewing content. The fifth tiled link 172 ("Medications") may include a medications listing area 216, with icons for adding or subtracting medications, and a timeline area 218 for tracking dates/times for taking medications. The sixth tiled link 174 ("Health Numbers") may include a data entry area 220 for inputting health numbers, along with links, for example, for updating the information and/or retrieving historical information. The seventh tiled link 176 ("Social") may include a social update area 222 for preparing statements, content, links or otherwise for sharing, as well as social links 224 for selecting social media outlets. The eight tiled link 178 ("Rewards") may include a rewards area 226 for tracking rewards and incentives.

A link from various sources, such as from the events/reminders in the banner 154, the daily check-in module, the health numbers module, or the like, may lead to displaying the measurement result 72 described above with respect to FIG. 3. For example, a pop-up window 230, specific to the individual 70, may be displayed upon selecting one of the aforementioned links, along with related program data and content 232 which may correspond to the measurement result 72.

Alternative embodiments may implement various features described above in hardware and/or software and with varying levels of integration. In addition, alternative embodiments may combine or further separate or distribute hardware elements, or software elements, as may be appropriate for the task.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

What is claimed is:

1. A horizontally integrated electronic system for administering a health services program executable on an electronic computer according to a program stored in a non-transient medium to implement:
a plurality of modules, including:
a video conferencing module configured to enable live video conferencing sessions over a computer network;
a health services module configured to index a plurality of health services content; and
a scheduling module configured to receive scheduling information relating to a plurality of time slots for health services; and
a rules engine in communication with each of the plurality of modules, wherein the rules engine is configured to implement a common hierarchy with respect to each module by monitoring for an event in each module and propagating an update to any other module when triggered by an event that occurs in the module, and
wherein the rules engine is configured to receive an identification code and selectively limit the health services module to delivering an allowable group of health services content from the plurality of health services content that is pre-approved for the identification code when triggered by an event that occurs in another module.

2. The system of claim 1, wherein the event is starting a video conferencing session via the video conferencing module, and the rules engine updates the health services module to deliver content related to the video conferencing session.

3. The system of claim 2, wherein the content is an informational article.

4. The system of claim 2, wherein the video conferencing session is a one-to-many group session.

5. The system of claim 1, wherein the event is a selection of content via the health services module, and the rules engine updates the video conferencing module to suggest a video conferencing session to join.

6. The system of claim 1, wherein the event is a selection of a time slot via the scheduling module, and the rules engine updates the health services module to deliver content related to the selection.

7. The system of claim 1, wherein the event is a selection of a time slot via the scheduling module, and the rules engine updates the video conferencing module to initiate a timer for countdown to a live video conferencing session according to the selection of the time slot.

8. The system of claim 1, wherein the event is a video conferencing session via the video conferencing module, and the rules engine updates the scheduling module to record a completion of the video conferencing session.

9. The system of claim 1, wherein the event is a selection of content via the health services module, and the rules engine updates the scheduling module to suggest a time slot related to the selection.

10. The system of claim 1, wherein the rules engine is further configured to arrange a plurality of content and time slots with respect to a timeline via a graphical display.

11. The system of claim 1, wherein the plurality of odules are further configured to communicate via an Application Program Interface (API).

12. The system of claim 1, wherein the rules engine is further configured to graphically display a plurality of health services activities, including at least one of a live video conferencing session and health services content, with respect to a common timeline.

13. The system of claim 12, wherein the rules engine updates a health services activity according to an event that occurs in at least one of the plurality of modules.

14. A method for administering a health services program from an electronic computer providing a video conferencing module configured to enable live video conferencing sessions over a computer network, a health services module configured to index a plurality of health services content, and a scheduling module configured to receive scheduling information relating to a plurality of time slots for health services, the method comprising:
   monitoring an event that occurs in a first module, the first module being at least one of the video conferencing module, the health services module and the scheduling module; and
   implement a common hierarchy with respect to each module by monitoring for an event in each module and propagating an update related to the event to second and third modules when triggered by the event, the second and third modules being at least two of the video conferencing module, the health services module and the scheduling module and being different from the first module, so that each module is connected at a common hierarchy level,
   wherein the rules engine is configured to receive an identification code and selectively limit the health services module to delivering an allowable up of health services content from the plurality of health services content that is pre-approved for the identification code when triggered by an event that occurs in another module.

15. The method of claim 14, wherein the first module is the health services module, the second module is the video conferencing module, the event is selecting content, and the update is suggesting a video conferencing session to join.

16. The method of claim 14, wherein the first module is the scheduling module, the second module is the health services module, the event is selecting a time slot, and the update is delivering content related to the selection.

17. The method of claim 14, wherein the first module is the scheduling module, the second module is the video conferencing module, the event is selecting a time slot, and the update is initiating a timer for countdown to a live video conferencing session according to the selection of the time slot.

18. An electronic system for building a curriculum providing health services, comprising:
   a plurality of modules, including:
      a video conferencing module configured to enable simultaneous live video conferencing sessions over multiple ports on a computer network;
      a health services module configured to index a plurality of health services content; and
      a scheduling module configured to receive scheduling information relating to a plurality of time slots for health services;
   a rules engine in communication with each of the plurality of modules, wherein the rules engine is configured to implement a common hierarchy with respect to each module by monitoring for an event in each module and propagating an update to any other module when triggered by an event that occurs in the module,
   wherein the rules engine is configured to receive an identification code and selectively limit the health services module to delivering an allowable group of health, services content from the plurality of health services content that, is pre-approved for the identification code when triggered by an event that occurs in another module; and
   an electronic computer executing a health services program stored in a non-transient medium to:
   receive a selection for a first health services program that includes a first set of health services activities including at least one live video conferencing session and at least one informational article;
   graphically display the first set of health services activities with respect to a timeline;
   receive a selection for a second health services program that includes a second set of health services activities including at least one live video conferencing session, the second health services program being different from the first health services program; and
   graphically display the second set of health services activities with respect to the timeline,
   wherein the first and second sets of health services activities are grouped with respect to the timeline.

19. The system of claim 18, wherein the second set of health services activities further includes at least one informational article.

20. The system of claim 18, wherein the health services activities are graphically displayed with a color code corresponding to an activity type.

21. The system of claim 18, wherein at least one of the health services activities includes hyperlink for further information about the respective health services activity.

* * * * *

UNITED STATES PATENT AND TRADEMARK OFFICE
CERTIFICATE OF CORRECTION

PATENT NO.          : 10,380,322 B2                     Page 1 of 1
APPLICATION NO.     : 14/608988
DATED               : August 13, 2019
INVENTOR(S)         : William Van Wyck et al.

It is certified that error appears in the above-identified patent and that said Letters Patent is hereby corrected as shown below:

In the Claims

Claim 11, Column 15, Line 12      Delete "odules" and substitute therefor --modules--.

Claim 14, Column 15, Line 46      Delete "up" and substitute therefor --group--.

Claim 18, Column 16, Line 28      Delete the "," after "that".

Signed and Sealed this
Seventeenth Day of December, 2019

Andrei Iancu
*Director of the United States Patent and Trademark Office*